(12) United States Patent
Arbiser et al.

(10) Patent No.: US 12,233,087 B2
(45) Date of Patent: Feb. 25, 2025

(54) PALLADIUM HYALURONIC ACID PARTICLES AND METHODS OF MANAGING CANCER OR ANGIOGENIC CONDITIONS

(71) Applicants: Emory University, Atlanta, GA (US); The United States Government represented by The United States Department of Veterans Affairs, Washington, DC (US)

(72) Inventors: Jack Arbiser, Atlanta, GA (US); Lily Yang, Atlanta, GA (US)

(73) Assignees: Emory University, Atlanta, GA (US); The United States Government represented byt The United States Department of Veterans Affairs, Atlanta, GA (US)

( * ) Notice: Subject to any disclaimer, the term of this patent is extended or adjusted under 35 U.S.C. 154(b) by 1053 days.

(21) Appl. No.: 17/055,945

(22) PCT Filed: May 16, 2019

(86) PCT No.: PCT/US2019/032605
§ 371 (c)(1),
(2) Date: Nov. 16, 2020

(87) PCT Pub. No.: WO2019/222461
PCT Pub. Date: Nov. 21, 2019

(65) Prior Publication Data
US 2023/0099637 A1 Mar. 30, 2023

Related U.S. Application Data

(60) Provisional application No. 62/672,280, filed on May 16, 2018.

(51) Int. Cl.
| | |
|---|---|
| A61K 33/24 | (2019.01) |
| A61K 9/00 | (2006.01) |
| A61K 9/06 | (2006.01) |
| A61K 9/20 | (2006.01) |
| A61K 31/56 | (2006.01) |
| A61K 31/728 | (2006.01) |
| A61P 35/00 | (2006.01) |

(52) U.S. Cl.
CPC ............ *A61K 33/24* (2013.01); *A61K 9/0056* (2013.01); *A61K 9/06* (2013.01); *A61K 9/20* (2013.01); *A61K 31/56* (2013.01); *A61K 31/728* (2013.01); *A61P 35/00* (2018.01)

(58) Field of Classification Search
None
See application file for complete search history.

(56) References Cited

U.S. PATENT DOCUMENTS

| 8,030,299 B2 | 10/2011 | Arbiser |
| 2015/0250892 A1 | 9/2015 | Amiji |
| 2015/0252120 A1 | 9/2015 | Di Pietro |
| 2017/0106630 A1 | 4/2017 | Suzuki |
| 2017/0172863 A1 | 6/2017 | Richard |

FOREIGN PATENT DOCUMENTS

| WO | 2003000190 | 1/2003 |
| WO | 2008076965 | 6/2008 |
| WO | 2017106630 | 6/2017 |

OTHER PUBLICATIONS

Bhandarkar et al. Tris (dibenzylideneacetone) dipalladium (Tris DBA), an N-myristoyltransferase 1 inhibitor, is effective against melanoma growth in vitro and in vivo, Clin Cancer Res 2008;14(5743-18).
Bonner et al. Honokiol bis-dichloroacetate (Honokiol DCA) demonstrates activity in vemurafenib-resistant melanoma in vivo, Oncotarget, 2016, 7(11):12857-68.
Cardenas-Trivino et al. Synthesis and Bactericidal Properties of Hyaluronic Acid Doped with Metal Nanoparticles, Journal of Nanomaterials, vol. 2017, Article ID 9573869, 9 pages.
Diaz et al. Tris DBA palladium is highly effective against growth and metastasis of pancreatic cancer in an orthotopic model, Oncotarget, 2016, 7(32):51569-51580.
Extended European Search Report, Application 19803007.4, dated Jan. 1, 2022.
Elsey et al. Palladium based nanoparticles for the treatment of advanced melanoma, Sci Rep 9, 3255 (2019).
Hayward et al. Hyaluronic acid-conjugated liposome nanoparticles for targeted delivery to CD44 overexpressing glioblastoma cells, Oncotarget, vol. 7, No. 23, 2016.
Kay et al. Tris (dibenzylideneacetone) Dipalladium: A Small-Molecule Palladium Complex Is Effective in Inducing Apoptosis in Chronic Lymphocytic Leukemia B-Cells, Leuk Lymphoma. 2016, 57(10): 2409-2416.
Mattheolabakis et al. Hyaluronic acid targeting of CD44 for cancer therapy: from receptor biology to hanomedicine, Journal of Drug Targeting, 2015, 23:7-8, 605-618.
Mero et al. Hyaluronic Acid Bioconjugates for the Delivery of Bioactive Molecules, Polymers 2014, 6, 346-369.
Parhi et al. Cross-Linked Hydrogel for Pharmaceutical Applications: A Review, Adv Pharm Bull, 2017, 7(4), 515-530.
Puente et al. Tris DBA palladium overcomes hypoxia-mediated drug resistance in multiple myeloma, Leuk Lymphoma. 2016, 57(7): 1677-1686.

(Continued)

*Primary Examiner* — Robert A Wax
*Assistant Examiner* — Quanglong N Truong
(74) *Attorney, Agent, or Firm* — Emory Patent Group (57) ABSTRACT

This disclosure relates to palladium hyaluronic acid particles such as dibenzylideneacetone palladium hyaluronic acid particles. In certain embodiments, this disclosure relates to methods of managing cancer or angiogenic conditions using particles disclosed herein and pharmaceutical compositions comprising the same. In certain embodiments, an objective of this disclosure is hyaluronic acid targeting of CD44, a tumor stem cell marker. In certain embodiments, this disclosure relates to treatment with hyaluronic acid palladium particles disclosed herein for depleting CD44 cells.

20 Claims, 3 Drawing Sheets

(56) References Cited

OTHER PUBLICATIONS

Rao et al. Palladium Based Nanoparticles for the Treatment of Advanced Melanoma, Annual Meeting of the International investigative Dermatology, J Invest Dermat, 2018.

Thinon et a. Global profiling of co- and post-translationally N-myristoylated proteomes in human cells, Nature Communications, 2014, 5:4919.

Wang et al. The Role of CD44 and Cancer Stem Cells, Cancer Stem Cells: Methods and Protocols, Methods in Molecular Biology, vol. 1692, Springer Science+Business Media LLC 2018.

Yoshida et al. Expression of insulin-like growth factor-1 receptor in metastatic uveal melanoma and implications for potential autocrine and paracrine tumor cell growth, Pigment Cell Melanoma Res, 2013, 27; 297-308.

Zhang et al. Activatable Hyaluronic Acid Nanoparticle as a Theranostic Agent for Optical/Photoacoustic Image-Guided Photothermal Therapy, ACS Nano 2014, 8, 12, 12250-12258.

Kallemeijn et al. Validation and Invalidation of Chemical Probes for the Human N-myristoyltransferases Jun. 20, 2019.

|  | Control | Free Tris DBA Palladium | Tris DBA Palladium -HANP | TrisDBA Palldium -HANP-αIGFR1 |
|---|---|---|---|---|
| Upregulated | -- | GAGE1 | LINC01419 | MIR4451 |
|  | -- | MIR518D | IGHD | MIR1224 |
|  | -- | MIR130B | MIR3147 | MIR4655 |
|  | -- | MIR3158-1 | MIR4655 | MIR1224 |
|  | -- | CCL7 | MIR4655 | MIR130B |
|  | -- | MIR3147 | SNORD114-28 | LPAL2 |
|  | -- | TFPI2 | C5orf46 | TTTY18 |
|  | -- | LINC01419 | HMCN1 | IGLC1 |
|  | -- | MIR1271 | SIGLEC17P | CYP2B6 |
|  | -- | SNORD114-13 | SPAG1 | DUX4 |
|  | -- | SNORD114-1 | MIR376A2 | OR10G7 |
|  | -- | LYZL2 | OR10G7 | TREML5P |
|  | -- | HSFY1P1 | EGR1 | MIR3187 |
|  | -- | YME1L1 | OR13C5 | OR1D4 |
|  | -- | RNF150 | MIR3201 | CD300LF |
| Downregulated | -- | SNORD115-38 | SNORA38B | MIR4279 |
|  | -- | ACTBL2 | ACTBL2 | MIR1321 |
|  | -- | ATP2A1 | STEAP1 | MSX2P1 |
|  | -- | MIR4500 | MIR4501 | MIR3170 |
|  | -- | MIR548AK | MMP1 | OR4N2 |
|  | -- | SCG2 | SCG2 | MIRLET7A2 |
|  | -- | DPT | MIR4500 | MIR4716 |
|  | -- | LINC01284 | GOLGA6L4 | MIR548AD |
|  | -- | NEAT1 | MIR4469 | GOLGA6L4 |
|  | -- | MIR4501 | SCGB2B3P | MIR519E |
|  | -- | MIR125B1 | MIR4436A | KRTAP20-1 |
|  | -- | MYH1 | POTEA | MIR4501 |
|  | -- | GOLGA6L4 | MIR4530 | SNORD114-4 |
|  | -- | PLK2 | TRIM77 | OR6C75 |
|  | -- | HSPA9 | PRAMEF2 | LAIR2 |

FIG. 4

PALLADIUM HYALURONIC ACID PARTICLES AND METHODS OF MANAGING CANCER OR ANGIOGENIC CONDITIONS

CROSS-REFERENCE TO RELATED APPLICATIONS

This application is the National Stage of International Application No. PCT/US2019/032605 filed May 16, 2019, which claims the benefit of U.S. Provisional Application No. 62/672,280 filed May 16, 2018. The entirety of each of these applications is hereby incorporated by reference for all purposes.

STATEMENT REGARDING FEDERALLY SPONSORED RESEARCH OR DEVELOPMENT

This invention was made with government support under BX002926 awarded by the National Institutes of Health. The government has certain rights in the invention.

BACKGROUND

Metastatic melanoma remains a leading cause of morbidity and mortality. Targeted therapy has been limited to BRAF mutant melanoma, and even dual MEK/BRAF blockade leads to efficacy for short periods of time, likely due to activation of alternative signaling pathways. Melanomas that arise after BRAF blockade are often highly aggressive, and there is no targeted therapy against NRAS melanoma, triple negative melanoma, ocular melanoma and other subtypes. Thus, improved therapies are needed.

Bhandarkar et al. report tris (dibenzylideneacetone) dipalladium, a N-myristoyltransferase-1 inhibitor, is effective against melanoma growth. Clin Cancer Res. 2008, 14:5743-5748. See also U.S. Pat. No. 8,030,299, and Diaz et al. Tris DBA palladium is highly effective against growth and metastasis of pancreatic cancer in an orthotopic model, and Puente et al., Tris (dibenzylideneacetone) dipalladium overcomes hypoxia-mediated drug resistance in multiple myeloma. Leuk Lymphoma, 2016, 57(7):1677-86. However, the usefulness of tris DBA Pd is limited by poor solubility. Thus, there is a need to identify improved therapies.

LM36 and LM36R are melanoma cell lines. LM36R differs from LM36 in that LM36R has acquired vemurafenib resistance. See Bonner et al. Oncotarget. 2016; 7:12857-12868.

Mero et al. report hyaluronic acid bioconjugates for the delivery of bioactive molecules. Polymers 2014, 6, 346-369.

Wang et al. report a role of CD44 in cancer. Methods Mol Biol. Chapter 3, 2018, 1692:31-42.

References cited herein are not an admission of prior art.

SUMMARY

This disclosure relates to palladium hyaluronic acid particles such as dibenzylideneacetone palladium hyaluronic acid particles. In certain embodiments, this disclosure relates to methods of managing cancer or angiogenic conditions using particles disclosed herein and pharmaceutical compositions comprising the same. In certain embodiments, an objective of this disclosure is hyaluronic acid targeting of CD44, a tumor stem cell marker. In certain embodiments, this disclosure relates to treatment with hyaluronic acid palladium particles disclosed herein for depleting CD44 cells.

In certain embodiments, this disclosure relates to compositions comprising dibenzylideneacetone palladium and hyaluronic acid, and optionally further comprising a lipid covalently conjugated to the hyaluronic acid. In certain embodiments, the hyaluronic acid is covalently conjugated to a lipophilic group such as a polycyclic non-aromatic hydrocarbon, steroid, steroid/bile acid, or long chain fatty acid. In certain embodiments, the lipid is a polycyclic hydrocarbon or steroid acid. In certain embodiments, particles are made by the process of mixing a dibenzylideneacetone palladium and hyaluronic acid in a homogenizer.

In certain embodiments, the disclosure contemplates particle compositions and uses thereof wherein the particles are absent additional targeting agents, e.g. Tris DBA-Pd hyaluronic acid nanoparticles in the absence of a targeting agent conjugated to the surface of the nanoparticles.

In certain embodiments, mixing is forcing a mixture of a dibenzylideneacetone palladium and hyaluronic acid through a narrow gap at pressure above 5, 50, 100, 150, 200, 250, 300, or 350 MPa. Typically, the homogenized palladium hyaluronic acid particles result in an average dimeter of less than 1 millimeter, 1 micrometer, or less than 500, 200, or 100 nanometers and greater than 10, 5, or 3 nanometers.

In certain embodiments, the palladium hyaluronic acid particles are made by the process of linking a lipophilic moiety to hyaluronic acid to form particles, and the particles are then mixed with tris (dibenzylideneacetone) palladium or other (dibenzylideneacetone) palladium complexes under conditions such that palladium and/or dibenzylideneacetone palladium is impregnated into the hyaluronic acid particles providing palladium hyaluronic acid particles and/or the dibenzylideneacetone palladium hyaluronic acid particles. Typically, the palladium hyaluronic acid particles and/or the dibenzylideneacetone palladium hyaluronic acid particles are proceeded through a high-pressure homogenizer.

In certain embodiments, this disclosure relates to pharmaceutical compositions comprising palladium hyaluronic acid particles disclosed herein and a pharmaceutically acceptable excipient. In certain embodiments, the pharmaceutical composition is in the form of a tablet, pill, capsule, gel, gel capsule, or cream. In certain embodiments, the pharmaceutical composition is in the form of a sterilized pH buffered aqueous salt solution or a saline phosphate buffer between a pH of 6 to 8, optionally comprising a saccharide or polysaccharide. In certain embodiments, the pharmaceutical composition is in solid form surrounded by an enteric coating. In certain embodiments, the enteric coatings comprises methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, or combinations thereof.

In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, corn starch, carnauba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

In certain embodiments, this disclosure relates to methods of treating or preventing cancer comprising administering an effective amount of palladium hyaluronic acid particles disclosed herein to a subject in need thereof. In certain embodiments, this disclosure relates to a medicament for uses in managing cancer as reported herein. In certain embodiments, this disclosure relates to the production of a medicament for uses in managing cancer as reported herein.

In certain embodiments, the disclosure relates to a pharmaceutical composition comprising palladium hyaluronic acid particles and further comprising a second therapeutic agent. In certain embodiments, the second therapeutic agent is an anti-cancer agent selected from abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed di sodium, copanli sib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof.

In certain embodiments, the disclosure relates to a method of treating or preventing cancer comprising administering an effective amount of palladium hyaluronic acid particles disclosed herein to a subject in need thereof. In certain embodiments, the subject is diagnosed with or at risk of cancer. In certain embodiments, the particles are administered in combination with a second therapeutic agent.

In certain embodiments, the disclosure relates to diagnosing and/or treating a subject diagnosed with cancer cells that express CD44 or increased expression of CD44 on a sample of cancer cells compared to a control, reference, or normal cells.

In certain embodiments, the subject is diagnosed with melanomas that have become resistant to Braf inhibitors.

In certain embodiments, the cancer is selected from multiple myeloma, bladder cancer, lung cancer, breast cancer, melanoma, colon and rectal cancer, non-Hodgkin lymphoma, Burkett lymphoma, endometrial cancer, pancreatic cancer, kidney cancer, prostate cancer, leukemia, thyroid cancer, and brain cancer.

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

"Subject" refers to any animal, preferably a human patient, livestock, rodent, monkey or domestic pet.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compared to a control without. It may also be identified by a change in relevant biomarker or gene expression profile, such as PSA for prostate cancer, HER2 for breast cancer, or others.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, idoxifene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Hyaluronic acid (HA) refers to a polymer of glucuronic acid and N-acetyl glucosamine or salts thereof, i.e., non-sulfated polymer of disaccharide containing glucuronic acid and glucosamine, and forms viscous aqueous solutions or gels with water. Naturally occurring hyaluronic acid can be obtained from connective tissues such as umbilical cord, synovial fluid, skin, tissues, and the vitreous body. Hyaluronic acid is typically reported with a molecular weight of $10^3$ to $10^7$. Pharmaceutical grade sodium hyaluronate may be fermented from Streptococcus zooepidemicus. Due to enzymatic degradation by hyaluronidases, the half-life of hyaluronate in endothelial tissue is less than a day. Chemical modification of HA can be performed on the three available functional sites of HA: the carboxylic, the hydroxyl and the acetamido groups. See Mero et al. Polymers 2014, 6, 346-369. HA crosslinking or conjugation maybe in water or in organic solvents, such as dimethylformamide (DMF) or dimethylsulfoxide (DMSO). HA sodium salt may be converted into either its acidic form or a tetrabutylammonium (TBA) salt for solubilization in organic solvents.

As used herein the term "dibenzylideneacetone palladium" refers to tris dibenzylideneacetone (DBA) dipalladium, monopalladium complexes, and combinations thereof. Pd(DBA)2 dissociates in solution giving the binuclear complex $Pd_2(DBA)_3$. A complex $Pd(DBA)_3$ forms by the addition of excess DBA to $Pd(DBA)_2$ indicating the existence of the reversible series of Pd-DBA complexes in solution. See Mazza et al., Palladium(0) Complexes of Dibenzylideneacetone. Formation and Molecular Structure of Tris(dibenzylideneacetone)palladium(0). Inorganic Chemistry, 1973, 12(12): 2955-2959. After homogenization, described below, it is contemplated that hyaluronic particles formed contain a form of dibenzylideneacetone palladium.

A homogenizer is a piece of equipment used for the homogenization of various types of material such as a blender. High-pressure homogenizers typically contain a high-pressure pump and a homogenizing nozzle to force a stream of a liquid sample through a system. The liquid and particles therein are subject to any one of a number of forces which is intended to homogenize the sample and/or reduce the size of particles within the liquid, e.g., by forcing a fluidic product through a narrow gap (the homogenizing nozzle) at high pressure (5-50 MPa, 50-150 MPa, 150-200

MPa, 200-350 MPa, or 350-400 MPa). Extreme shear and compression can be applied to reduce droplets from the micro- to the nano-scale range. Depending on the setup of a particular system, a high-pressure homogenizer could operate on any combination of shear forces, impact, and cavitation. Some setups provides for a tank to which high pressure is applied in order to force the liquid sample contained therein through a valve or membrane with very narrow slits. This act causes high shear, a large pressure drop, and cavitation, all of which act to homogenize the sample. Sometimes the high-pressure stream is directed at a blade, ring, or plate, upon which the sample collides at a high speed, to aid in homogenization.

As used herein, a "lipid" group refers to a hydrophobic group that is naturally or non-naturally occurring that is highly insoluble in water. As used herein a lipid group is considered highly insoluble in water when the point of connection on the lipid is replaced with a hydrogen and the resulting compound has a solubility of less than $0.63 \times 10^{-4}$ % w/w (at 25° C.) in water, which is the percent solubility of octane in water by weight. See Solvent Recovery Handbook, $2^{nd}$ Ed, Smallwood, 2002 by Blackwell Science, page 195. Examples of naturally occurring lipids include saturated or unsaturated hydrocarbon chains found in fatty acids, glycerolipids, cholesterol, steroids, polyketides, and derivatives. Non-naturally occurring lipids include derivatives of naturally occurring lipids, acrylic polymers, aromatic, and alkylated compounds and derivatives thereof.

A "linking group" refers to any variety of molecular arrangements that can be used to bridge to molecular moieties together. An example formula may be —$R_m$— wherein R is selected individually and independently at each occurrence as: —$CR_mR_m$—, —$CHR_m$—, —CH—, —C—, —$CH_2$—, —$C(OH)R_m$—, —C(OH)(OH)—, —C(OH)H, —$C(Hal)R_m$—, —C(Hal)(Hal)-, —C(Hal)H—, —$C(N_3)R_m$—, —$C(CN)R_m$—, —C(CN)(CN)—, —C(CN)H—, —$C(N_3)(N_3)$—, —$C(N_3)H$—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=$CH_2$, —CCH, —OH, —SH, —$NH_2$, —$N_3$, —CN, or -Halogen (Hal), or two branched Rs may form a cyclic structure. It is contemplated that in certain instances, the total Rs or "m" may be less than 100 or 50 or 25 or 10. Examples of linking groups include bridging alkyl, alkoxyalkyl groups, and polyalkoxy groups.

The terms "angiogenic disease", "angiogenic disorder" and "angiogenic skin disorder" is used throughout the specification to describe a disorder, generally a skin disorder or related disorder which occurs as a consequence of or which results in increased vascularization in tissue. Oftentimes, the etiology of the angiogenic disease is unknown. However, whether angiogenesis is an actual cause of a disease state or is simply a condition of the disease state is unimportant, but the inhibition of angiogenesis in treating or reversing the disease state or condition is an aspect of the present disclosure.

The term "rosacea" is used to describe acne rosacea or erythematosa characterized by vascular and follicular dilation involving the nose and continuous portions of the cheeks. Rosacea may vary from very mild but persistent erythema to extensive hyperplasia of the sebaceous glands with deep-seated papules and pustules and accompanied by telangiectasia at the affected erythematous sites. Also called hypertrophic rosacea or rhinophyma, depending upon the severity of the condition.

The term "wart" is used to describe a small, usually hard tumorous growth on the skin. Also known as a verucca, a wart is a flesh-colored growth of the skin which is characterized by circumscribed hypertrophy of the papillae of the corium, with thickening of the malpighian, granulation and keratin layers of the epidermis. Verucca vulgaris, a subset of warts or verruca, is characterized by infection of the keratinocytes with human papillomavirus.

The term "psoriasis" is used to describe a skin condition which is characterized by the eruption of circumscribed, discrete and confluent, reddish, silvery-scaled maculopapular rash; the lesions occur preeminently on the elbows, knees, scalp and trunk and microscopically show characteristic parakeratosis and elongation of rete ridges.

The term "acne" is used to describe a condition of the skin characterized by inflammatory follicular, papular and pustular eruptions involving the sebaceous apparatus. Although there are numerous forms of acne, the most common form is known as acne simplex or acne vulgaris which is characterized by eruptions of the face, upper back and chest and is primarily comprised of comedones, cysts, papules and pustules on an inflammatory base. The condition occurs primarily during puberty and adolescence due to an overactive sebaceous apparatus which is believed to be affected by hormonal activity.

The term "eczema" is a generic term used to describe acute or chronic inflammatory conditions of the skin, typically erythematous, edematous, papular, vesicular, and crusting; followed often by lichenification and scaling and occasionally by duskiness of the erythema and, infrequently, hyperpigmentation. Eczema is often accompanied by the sensation of itching and burning. Eczema vesicles form by intraepidermal spongiosis. Eczema is sometimes referred to colloquially as tetter, dry tetter and scaly tetter. There are numerous subcategories of eczema, all of which are treated by one or more of the particles according to the present disclosure. Another term for eczema is atopic dermatitis.

Palladium Based Nanoparticles for the Treatment of Cancer and Related Conditions Tris(dibenzylideneacetone)dipalladium (Tris DBA-Pd) is reported to have activity against the enzyme N-myristoyl-transferase 1 (NMT1), which catalyzes myristoylation of proteins, including c-src, allowing membrane localization and attenuates MAP kinase, AKT, and STAT3 signaling. Tris DBA-Pd has in vitro efficacious against melanoma, and preclinical models of pancreatic cancer, chronic lymphocytic leukemia and multiple myeloma as well. See Diaz, B. et al. Tris DBA-Pd is highly effective against growth and metastasis of pancreatic cancer in an orthotopic model. Oncotarget, 7, 51569-51580, (2016), de la Puente, P. et al. Tris DBA-Pd overcomes hypoxia-mediated drug resistance in multiple myeloma. Leukemia & lymphoma 57, 1677-1686 (2016), and Kay, N. E. et al. Tris (dibenzylideneacetone) dipalladium: a small-molecule palladium complex is effective in inducing apoptosis in chronic lymphocytic leukemia B-cells. Leukemia & lymphoma 57, 2409-2416 (2016). Thus, this compound might have therapeutic benefit against a variety of cancers, and not limited to those with a specific mutation.

An obstacle to the clinical development of Tris (dibenzylideneacetone) dipalladium is its poor solubility. In order to overcome this obstacle, the drug was incorporated into targeted hyaluronic acid-based nanoparticles to target LM36R, a well-established human melanoma xenograft model of BRAF resistance. Two potential targets for our drug payload, CD44 and IGFR1 were examined. CD44 and IGFR1 are both implicated in the progression of metastatic melanoma. Hyaluronic acid targets receptor, CD44, which is expressed on melanoma stem cells and on aggressive tumor cells from multiple different types of tumors. IGF1R has been found to be upregulated in melanoma cells and is thought to be involved in numerous pathways that regulate cell survival and proliferation. Reports indicate treatment with anti-IGF1R antibody is able to reduce tumor growth in uveal melanoma. Yoshida et al. Expression of insulin-like growth factor-1 receptor in metastatic uveal melanoma and implications for potential autocrine and paracrine tumor cell growth. Pigment Cell Melanoma Res. 27(2), 297-308 (2014).

In certain embodiments, the disclosure relates to methods of treating or preventing cancer or angiogenic conditions comprising administering an effective amount of palladium hyaluronic acid particles disclosed herein to a subject in need thereof. In certain embodiments, the subject is diagnosed with or at risk of cancer. In certain embodiments, the particles are administered in combination with a second therapeutic agent.

In certain embodiments, an objective of this disclosure is hyaluronic acid targeting of CD44, a tumor stem cell marker, and that treatment with the hyaluronic acid palladium particles causes depletion of CD44 cells. In certain embodiments, the disclosure relates to the treatment of a subject diagnosed with cancer cells that express CD44 or increased expression of CD44 on a sample of cancer cells compared to normal cells. Wang et al. report CD44, and CD44v isoforms, are cancer stem cell (CSC) markers and detailed experimental methods regarding CD44+tumor cell isolation that can be used to identify subjects that will be responsive to treatment methods with the hyaluronic acid palladium particles as described herein. Methods Mol Biol. Chapter 3, 2018, 1692:31-42. CD44 gene contains central exons (known as "variable" exons) undergo extensive alternative splicing via inclusion or excision in various combinations to generate splicing variants (CD44v isoforms). The standard CD44 (CD44s) does not contain any variant exons, wherein CD44v contains at least one of the variant exons. In certain embodiments, the disclosure relates to the treatment of a subject diagnosed with cancer cells that express CD44s and/or CD44v.

In certain embodiments, the disclosure relates to the treatment of a subject diagnosed with cancer cells that express CD44v such as CD44v1, CD44v2, CD44v3, CD44v4, CD44v5, CD44v6, CD44v7, CD44v8, CD44v9, CD44v10, or combinations thereof.

In certain embodiments, the disclosure relates to the treatment of a subject diagnosed with cancer cells that express CD44v1. In certain embodiments, the disclosure relates to the treatment of a subject diagnosed with cancer cells that express CD44v2. In certain embodiments, the disclosure relates to the treatment of a subject diagnosed with cancer cells that express CD44v3. In certain embodiments, the disclosure relates to the treatment of a subject diagnosed with cancer cells that express CD44v4. In certain embodiments, the disclosure relates to the treatment of a subject diagnosed with cancer cells that express CD44v5. In certain embodiments, the disclosure relates to the treatment of a subject diagnosed with cancer cells that express CD44v6. In certain embodiments, the disclosure relates to the treatment of a subject diagnosed with cancer cells that express CD44v7. In certain embodiments, the disclosure relates to the treatment of a subject diagnosed with cancer cells that express CD44v8. In certain embodiments, the disclosure relates to the treatment of a subject diagnosed with cancer cells that express CD44v9. In certain embodiments, the disclosure relates to the treatment of a subject diagnosed with cancer cells that express CD44v10.

In certain embodiments, in a subject with cancer, methods disclose herein comprise measuring an increased level of CD44s, CD44v1, CD44v2, CD44v3, CD44v4, CD44v5, CD44v6, CD44v7, CD44v8, CD44v9, CD44v10, or combinations thereof in a cancer cell compared to a control or normal reference value, and diagnosing the subject as responsive to palladium hyaluronic acid particle treatments disclosed herein, and thereby administering the palladium hyaluronic acid particles to the subject.

In certain embodiments, in a subject with colon cancer, methods disclose herein comprise measuring an increased level of CD44s, CD44v1, CD44v2, CD44v3, CD44v4, CD44v5, CD44v6, CD44v7, CD44v8, CD44v9, CD44v10, or combinations thereof in a breast compared to a control or normal reference value, and diagnosing the subject as responsive to any of the palladium hyaluronic acid particle treatments disclosed herein, and thereby administering the palladium hyaluronic acid particles to the subject.

In certain embodiments, in a subject with colon cancer, methods disclose herein comprise measuring an increased level of CD44v6 in a cancer cell compared to a control or normal reference value, and diagnosing the subject as responsive to any of the palladium hyaluronic acid particle treatments disclosed herein, and thereby administering the palladium hyaluronic acid particles to the subject.

In certain embodiments, in a subject with gastric cancer, methods disclose herein comprise measuring an increased level of CD44v8, CD44v9, CD44v10, or combinations thereof in a cancer cell compared to a control or normal reference value, and diagnosing the subject as responsive to any of the palladium hyaluronic acid particle treatments disclosed herein, and thereby administering the palladium hyaluronic acid particles to the subject.

In certain embodiments, in a subject with head or neck cancer, methods disclose herein comprise measuring an increased level of CD44v3 in a cancer cell compared to a control or normal reference value, and diagnosing the subject as responsive to any of the palladium hyaluronic acid particle treatments disclosed herein, and thereby administering the palladium hyaluronic acid particles to the subject.

In certain embodiments, measuring an increased level of CD44s, CD44v1, CD44v2, CD44v3, CD44v4, CD44v5, CD44v6, CD44v7, CD44v8, CD44v9, CD44v10, or combinations thereof, is individually or in combination with other marker(s) such as CD24, CD133, CD34, and c-Met.

In certain embodiments, the cancer is selected from bladder cancer, lung cancer, breast cancer, melanoma, colon and rectal cancer, non-Hodgkin lymphoma, Burkett lymphoma, endometrial cancer, pancreatic cancer, kidney cancer, prostate cancer, leukemia, thyroid cancer, head and neck cancer, glioma, glioblastoma, and brain cancer.

In certain embodiments, this disclosure relates to methods of treating cancer comprising administering an effective amount of palladium hyaluronic acid particles disclosed herein to a subject in need thereof. In certain embodiments, the subject is suffering from a neoplasm. In certain embodiments, the neoplasm has a mutation encoding a V600E amino acid substitution present in the coding sequence for BRAF or other mutation. In certain embodiments, the subject is suffering from metastatic melanoma.

In certain embodiments, the subject is diagnosed with cancer or hematological malignancy. In certain embodiments, the hematological malignancy is multiple myeloma, leukemia, or lymphoma. In certain embodiments, the hematological malignancy is acute lymphoblastic leukemia (ALL), acute myelogenous leukemia (AML), chronic lymphocytic leukemia (CLL), small lymphocytic lymphoma (SLL), chronic myelogenous leukemia, acute monocytic leukemia (AMOL), Hodgkin's lymphomas, and non-Hodgkin's lymphomas such as Burkitt lymphoma, B-cell lymphoma.

In certain embodiments, the palladium hyaluronic acid particles disclosed herein are administered in combination with a second anticancer agent. In certain embodiments, the second therapeutic agent is an anti-cancer agent. In certain embodiments, the second therapeutic agent is a BRAF inhibitor. In certain embodiments, the BRAF inhibitor is vemurafenib, sorafenib, encorafenib, and dabrafenib.

Accordingly, palladium hyaluronic acid particles disclosed herein may be used in the treatment of a neoplasm, particularly a susceptible neoplasm (a cancer or tumor) in a mammal. The present disclosure also provides a method for treating a neoplasm, particularly a susceptible neoplasm in a mammal in need thereof, which method comprises administering to the mammal a therapeutically effective amount of the particles disclosed herein. In certain embodiments, the disclosure also provides the use of palladium hyaluronic acid particles disclosed herein for the preparation of a medicament for the treatment of neoplasm, particularly a susceptible neoplasm, in a mammal.

In certain embodiment, this disclosure relates to methods for the treatment a subject at risk of, exhibiting symptoms of, suspected of, or diagnosed with a cancer or neoplasm selected from skin cancer, melanoma, Barret's adenocarcinoma; biliary tract carcinomas; breast cancer; cervical cancer; cholangiocarcinoma; central nervous system tumors including primary CNS tumors such as glioblastomas, astrocytomas (including glioblastoma multiforme) and ependymomas, and secondary CNS tumors (i.e., metastases to the central nervous system of tumors originating outside of the central nervous system), colorectal cancer, including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; and thyroid cancers.

In certain embodiments, this disclosure relates to the use of palladium hyaluronic acid particles disclosed herein for the preparation of a medicament for the treatment of Barret's adenocarcinoma; biliary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers, or any subset thereof, in a mammal (e.g., human).

The particles disclosed herein can be used alone in the treatment of each of the foregoing conditions or can be used to provide additive or potentially synergistic effects with certain existing chemotherapies, radiation, biological or immunotherapeutics (including monoclonal antibodies) and vaccines. The palladium hyaluronic acid particles disclosed herein may be useful for restoring effectiveness of certain existing chemotherapies and radiation and or increasing sensitivity to certain existing chemotherapies and/or radiation.

In certain embodiments, this disclosure provides a method for treating a susceptible neoplasm in a mammal in need thereof comprising the steps of: (a) analyzing a sample from said neoplasm to determine whether an activating mutation is present in the coding sequence for BRAF in cells of said neoplasm; (b) selecting a mammal having a neoplasm with an activating mutation in the coding sequence for BRAF; and (c) administering a therapeutically effective amount of palladium hyaluronic acid particles disclosed herein to the mammal selected in step (b).

In certain embodiments, the activating mutation present in the coding sequence for BRAF results in a BRAF having an amino acid substitution selected from the group consisting of R462I, I463S, G464V, G464E, G466A, G466E, G466V, G469A, G469E, D594V, F595L, G596R, L597V, L597R, T5991, V600E, V600D, V600K, V600R, T119S, and K601E. See, for example, FIG. 2 of Halilovic and Solvit (2008) Current Opinion in Pharmacology 8:419-26.

In certain embodiments, this disclosure relates to a method for treating a susceptible neoplasm in a mammal in need thereof comprising the steps of: (a) analyzing a sample from said neoplasm to determine whether a mutation encoding a V600E, V600D or V600R amino acid substitution is present in the coding sequence for BRAF in cells of said neoplasm; (b) selecting a mammal having a neoplasm with a mutation encoding the V600E, V600D or V600R amino acid substitution in BRAF; and (c) administering a therapeutically effective amount of palladium hyaluronic acid particles disclosed herein to the mammal selected in step (b).

The V600E amino acid substitution in BRAF is described, for example, in Kumar et al. (2004) J Invest Dermatol. 122(2):342-8. This mutation commonly results from a T1799A mutation in the coding sequence for human BRAF. Accordingly, in one embodiment of the present disclosure, the step of analyzing a sample from said neoplasm to determine whether a mutation encoding a V600E amino acid substitution is present in the coding sequence for BRAF is performed by determining whether the coding sequence for BRAF in cells of the neoplasm contains the T1799A mutation.

In one preferred embodiment, the neoplasm is melanoma.

In particular embodiments, the neoplasm is selected from breast cancer, cholangiocarcinoma, colorectal cancer, melanoma, non-small cell lung cancer, ovarian cancer, and thyroid cancer.

In certain embodiments, the subject is a mammal such as a human.

The sample of the neoplasm to be analyzed for the presence of BRAF activating mutations can be derived from a variety of sources including, but not limited to, single cells, a collection of cells, tissue, cell culture, bone marrow, blood, or other bodily fluids. The tissue or cell source may include a tissue biopsy sample, a cell sorted population, cell culture, or a single cell. In selecting a sample, the percentage of the sample that constitutes neoplastic cells should be considered. In some embodiments, the sample from the neoplasm is fixed using a preservative prior to analyzing for the presence of an activating mutation.

The step of analyzing a sample from the neoplasm to determine whether an activating mutation is present in the coding sequence for BRAF in cells of said neoplasm may be performed using any method known in the art. For example, the coding sequence for BRAF in cells of the sample may be analyzed to determine if it contains a mutation which results in the expression of activated BRAF. Methods for detecting such mutations are well known in the art. See, for example, Whitcombe et al. (1999) Nature Biotechnology 17:804-7, Gibson (2006) Clinica Chimica Acta 363: 32-47, Kim and Misra (2007) Annual Review of Biomedical Engineering 9:289-320, and U.S. Pat. Nos. 6,326,145 and 6,270,967). Alternatively, activating mutations in BRAF may be identified by directly detecting the activated BRAF protein using an agent (e.g. an antibody) that selectively binds activated BRAF.

The precise therapeutically effective amount of palladium hyaluronic acid particles disclosed herein will depend on a number of factors. There are variables inherent to the particles including, but not limited to, the following: molecular weight, absorption, bioavailability, distribution in the body, tissue penetration, half-life, metabolism, protein binding, and excretion. These variables determine what dose of particles needs to be administered in a sufficient percentage and for a sufficient amount of time to have the desired effect on the condition being treated (e.g., neoplasm). The duration of drug exposure will be limited only by the particles half-life, and side effects from treatment requiring cessation of dosing. The amount of particles administered will also depend on factors related to patients and disease including, but not limited to, the following: the age, weight, concomitant medications and medical condition of the subject being treated, the precise condition requiring treatment and its severity, the nature of the formulation, and the route of administration. Ultimately, the dose will be at the discretion of the attendant physician or veterinarian. Typically, the particles disclosed herein will be given for treatment in the range of 0.01 to 30 mg/kg body weight of recipient (mammal) per day or per dose or per cycle of treatment and more usually in the range of 0.1 to 10 mg/kg body weight per day or per dose or per cycle of treatment. Thus, for an adult human being treated for a condition, the actual amount per day or per dose or per cycle of treatment would usually be from 1 to 2000 mg and this amount may be given in a single dose or multiple doses per day or per dose or per cycle of treatment. The full spectrum of dosing regimens may be employed ranging from continuous dosing (with daily doses) to intermittent dosing.

Palladium hyaluronic acid particles disclosed herein may also be used alone or in combination with a BRAF inhibitor or agonist in the treatment of conditions inhibited or attenuated by inhibition of a Raf family kinase (particularly BRAF). Further provided are methods for treating a condition attenuated by inhibition of a Raf family kinase (particularly BRAF) in a mammal in need thereof, comprising administering to the mammal, a therapeutically effective amount of particles disclosed herein. Also provided is the use of particles disclosed herein for the preparation of a medicament for the treatment of a condition attenuated by inhibition of a Raf family kinase (particularly BRAF) in a mammal. Conditions attenuated by inhibition of a Raf family kinase (including BRAF) include but are not limited to neoplasms.

In the above-described methods of treatment and uses, particles disclosed herein may be employed alone, in combination with one or more other compounds disclosed herein or in combination with other therapeutic methods or agents. In particular, in methods of treating a condition attenuated by combination with other chemotherapeutic, biologic, hormonal, antibody and supportive care agents is envisaged as well as combination with surgical therapy and radiotherapy. Supportive care agents include analgesics, anti-emetics and agents used to treat hematologic side effects such as neutropenia. Analgesics are well known in the art. Anti-emetics include but are not limited to $5HT_3$ antagonists such as ondansetron, granisetron, dolasetron, palonosetron and the like; prochlorperazine; metoclopramide; diphenhydramine; promethazine; dexamethasone; lorazepam; haloperidol; dronabinol; olanzapine; and neurokinin-1 antagonists such as aprepitant, fosaprepitant and casopitant administered alone or in various combinations.

Combination therapies according to the disclosure thus comprise the administration of particles disclosed herein and the use of at least one other treatment method. In one embodiment, combination therapies according to the disclosure comprise the administration of particles disclosed herein and surgical therapy. In one embodiment, combination therapies according to the disclosure comprise the administration of particles disclosed herein and radiotherapy. In one embodiment, combination therapies according to the disclosure comprise the administration of particles disclosed herein and at least one supportive care agent (e.g., at least one anti-emetic agent). In one embodiment, combination therapies according to the present disclosure comprise the administration of particles disclosed herein and at least one other chemotherapeutic agent. In one particular embodiment, the disclosure comprises the administration of particles disclosed herein and at least one anti-neoplastic agent.

As an additional aspect, the present disclosure provides the methods of treatment and uses as described above, which comprise administering particles disclosed herein together with at least one chemotherapeutic agent. In one particular embodiment, the chemotherapeutic agent is an anti-neoplastic agent. In another embodiment, the disclosure provides a pharmaceutical composition comprising particles disclosed herein further comprising at least one other chemotherapeutic agent, more particularly, the chemotherapeutic agent is an anti-neoplastic agent. The disclosure also provides methods of treatment and uses as described above, which comprise administering particles disclosed herein together with at least one supportive care agent (e.g., anti-emetic agent).

The particles disclosed herein and at least one additional anti-neoplastic or supportive care therapy may be employed in combination concomitantly or sequentially in any therapeutically appropriate combination. The administration of particles disclosed herein with one or more other anti-neoplastic agents may be in combination in accordance with the disclosure by administration concomitantly in one unitary pharmaceutical composition including particles and/or compounds or two or more separate pharmaceutical compositions each including one or more of the compounds or particles. The components of the combination may be administered separately in a sequential manner wherein one active ingredient is administered first and the other(s) second or vice versa. Such sequential administration may be close in time or remote in time.

When particles disclosed herein is used in combination with an anti-neoplastic and/or supportive care agent, the dose of each compound may differ from that when the compound is used alone. Appropriate doses will be readily appreciated by those skilled in the art. The appropriate dose of the particles disclosed herein and the other therapeutically active agent(s) and the relative timings of administration will be selected in order to achieve the desired combined therapeutic effect, and are within the expertise and discretion of the attendant clinician.

Typically, any chemotherapeutic agent that has activity against a susceptible neoplasm being treated may be utilized in combination with particles disclosed herein, provided that the particular agent is clinically compatible with therapy employing particles disclosed herein. Typical anti-neoplastic agents useful in the present disclosure include, but are not limited to: alkylating agents, anti-metabolites, antitumor antibiotics, antimitotic agents, topoisomerase I and II inhibitors, hormones and hormonal analogues; retinoids, signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Alkylating agents are non-phase specific anti-neoplastic agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Alkylating agents may be employed in combination with the particles disclosed herein in the compositions and methods described above. Examples of alkylating agents include but are not limited to nitrogen mustards such as cyclophosphamides, temozolomide, melphalan, and chlorambucil; oxazaphosphorines; alkyl sulfonates such as busulfan; nitrosoureas such as carmustine; triazenes such as dacarbazine; and platinum coordination complexes such as cisplatin, oxaliplatin and carboplatin.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. The end result of discontinuing S phase is cell death. Antimetabolite neoplastic agents may be employed in combination with the particles disclosed herein in the compositions and methods described above. Examples of antimetabolite anti-neoplastic agents include but are not limited to purine and pyrimidine analogues and anti-folate compounds, and more specifically, hydroxyurea, cytosine, arabinoside, raltitrexed, tegafur, fluorouracil (e.g., 5FU), methotrexate, cytarabine, mercaptopurine and thioguanine.

Antitumor antibiotic agents are non-phase specific agents, which bind to or intercalate with DNA. Typically, such action disrupts ordinary function of the nucleic acids, leading to cell death. Antitumor antibiotics may be employed in combination with the particles disclosed herein in the compositions and methods described above. Examples of antitumor antibiotic agents include, but are not limited to, actinomycins such as dactinomycin; anthracyclines such as daunorubicin, doxorubicin, idarubicin, epirubicin and mitoxantrone; mitomycin C and bleomycins.

Antimicrotubule or antimitotic agents are phase specific agents active against the microtubules of tumor cells during M or the mitosis phase of the cell cycle. Antimitotic agents may be employed in combination with the particles disclosed herein in the compositions and methods described above. Examples of antimitotic agents include, but are not limited to, diterpenoids, vinca alkaloids, polo-like kinase (Plk) inhibitors and CenpE inhibitors. Examples of diterpenoids include, but are not limited to, paclitaxel and its analog docetaxel. Examples of vinca alkaloids include, but are not limited to, vinblastine, vincristine, vindesine and vinorelbine. Plk inhibitors are discussed further below.

Topoisomerase inhibitors include inhibitors of Topoisomerase II and inhibitors of Topoisomerase I. Topoisomerase II inhibitors, such as epipodophyllotoxins, are anti-neoplastic agents derived from the mandrake plant, that typically affect cells in the S and G2 phases of the cell cycle by forming a ternary complex with topoisomerase II and DNA, causing DNA strand breaks. The strand breaks accumulate and cell death follows. Examples of epipodophyllotoxins include, but are not limited to, etoposide and teniposide. Camptothecins, including camptothecin and camptothecin derivatives, are available or under development as Topoisomerase I inhibitors. Examples of camptothecins include, but are not limited to amsacrine, irinotecan, topotecan, and the various optical forms of 7-(4-methylpiperazino-methylene)-10,11-ethylenedioxy-20-camptothecin. Topoisomerase inhibitors may be employed in combination with the particles disclosed herein in the compositions and methods described above.

Hormones and hormonal analogues are useful compounds for treating cancers in which there is a relationship between the hormone(s) and growth and/or lack of growth of the cancer. Antitumor hormones and hormonal analogues may be employed in combination with the particles disclosed herein in the compositions and methods described above. Examples of hormones and hormonal analogues believed to be useful in the treatment of neoplasms include, but are not limited to antiestrogens, such as tamoxifen, toremifene, raloxifene, fulvestrant, idoxifene and droloxifene; anti-androgens; such as flutamide, nilutamide, bicalutamide and cyproterone acetate; adrenocorticosteroids such as prednisone and prednisolone; aminoglutethimide and other aromatase inhibitors such as anastrozole, letrozole, vorozole, and exemestane; progestins such as megestrol acetate; 5alpha-reductase inhibitors such as finasteride and dutasteride; and gonadotropin-releasing hormones (GnRH) and analogues thereof, such as Luteinizing Hormone-releasing Hormone (LHRH) agonists and antagonists such as goserelin leuprolide, leuprorelin and buserelin.

Examples of specific retinoids that may be used in combination with the particles disclosed herein include: retinoic acid; all-trans-retinoic acid ("ATRA" also known as "tretinoin"); tamibarotene ("Am80"); 9-cis-retinoic acid ((2E,4E,6Z,8E)-3,7-Dimethyl-9-(2,6,6-trimethylcyclohex-1-enyl)nona-2,4,6,-8-tetraenoic Acid) (also known as "9-cis-Tretinoin") (available from Sigma); Isotretinoin ((2Z,4E,6E,8E)-3,7-dimethyl-9-(2,6,6-trimethyl-1-cyclohexenyl)nona-2,4,6,-8-tetraenoic acid) (also known as "13-cis-retinoic acid") (ACCUTANE™); Am580 (4-(5,6, 7,8-tetrahydro-5, 5,8, 8-tetramethyl-2-naphtamido) benzoic acid), See, M. Gianni, Blood 1996 87(4):1520-1531; TTNPB (4-[E-2-(5, 6,7,8-Tetrahydro-5,5,8,8-tetramethyl-2-naphthalenyl)-1-propeny-1]benzoic acid) (also known as "Ro 13-7410") See, M. F. Boehm et al. J. Med. Chem. 1994 37:2930 and R. P. Bissonnette et al., Mol. Cell. Biol. 1995 15:5576; and BMS753 (4-[[(2,3 -dihydro-1,1,3,3-tetramethyl-2-oxo-1H-inden-5-yl)carbonyl]amino]-benzoic acid) See, U.S. Pat. No. 6,184,256.

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the particles disclosed herein in any of the compositions and methods/uses described herein. Trastuzumab is an example of an anti-erbB2 antibody inhibitor of growth factor function. One example of an anti-erbB1 antibody inhibitor of growth factor function is cetuximab. Bevacizumab is an example of a monoclonal antibody directed against VEGFR. Examples of small molecule inhibitors of epidermal growth factor receptors include but are not limited to lapatinib and erlotinib. Imatinib is one example of a PDGFR inhibitor. Examples of VEGFR inhibitors include pazopanib, ZD6474, AZD2171, PTK787, sunitinib and sorafenib.

In certain embodiments, particles disclosed herein can be used and formulated in combination with anti-cancer agents that are PD-1 antibodies such as nivolumab, pembrolizumab, pidilizumab, atezolizumab or CTLA-4 antibodies such as ipilimumab and tremelimumab.

In certain embodiments the particles of the present disclosure are used to treat benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, nonmelanoma skin cancer and precursor lesions (including basal cell carcinoma, squamous cell carcinoma, and actinic keratosis), acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with particles according to the present disclosure.

In certain embodiments, this disclosure relates to methods of treating angiogenic skin disorders including psoriasis, acne, rosacea, warts and eczema, among numerous others, including Sturge-Weber syndrome, and related conditions using one or more of the disclosed compositions are other aspects of the present disclosure. In addition, the present particles may be used to treat venous ulcers of the skin as well. These methods comprise administering an effective amount of particles according to the present disclosure to a patient in need of treatment or therapy.

Further aspects of the present disclosure relate to the use of the present compositions in the treatment of arthritis and chronic inflammatory diseases, including rheumatoid arthritis and osteoarthritis, among others, including lupus and scleroderma. These methods also are directed to the administration of effective amounts of particles according to the present disclosure to a patient in need of treatment or therapy.

In certain embodiments, angiogenic skin disorders which may be treated utilizing particles according to the present disclosure include, for example, psoriasis, acne, rosacea, warts, seborrheic dermatitis, eczema (atopic dermatitis), hemangiomas and lymphangiogenesis, among numerous others, including Sturge-Weber syndrome, neurofibromatosis, tuberous sclerosis, chronic inflammatory disease and arthritis. Any skin disorder which has as a primary or secondary characterization, increased vascularization, is considered an angiogenic skin disorder for purposes of the present disclosure and is amenable to treatment with particles according to the present disclosure.

Further aspects of the disclosure relates to the use of particles disclosed herein in the treatment of HIV. The HIV protein nef requires myristoylation for activity. Thus, in certain embodiments, this disclosure relates to methods of treating HIV comprising administering an effective amount of particles disclosed herein to a subject in need thereof, e.g., diagnosed with HIV.

Pharmaceutical Compositions

The particles of the present disclosure can be administered to a subject either alone or as a part of a pharmaceutical composition. In certain embodiments, the pharmaceutical composition is in the form of a tablet, pill, capsule, gel, gel capsule or cream. In certain embodiments, the pharmaceutical composition is in the form of a sterilized pH buffered aqueous salt solution or a saline phosphate buffer between a pH of 6 to 8, optionally comprising a saccharide or polysaccharide.

In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, corn starch, carnauba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

In certain embodiments, pharmaceutical composition is in solid form surrounded by an enteric coating. In certain embodiments, the enteric coatings comprises methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, or combinations thereof.

The pharmaceutical compositions of the present disclosure can be administered to subjects either orally, rectally, parenterally (intravenously, intramuscularly, or subcutaneously), intracisternally, intravaginally, intraperitoneally, intravesically, locally (powders, ointments, or drops), or as a buccal or nasal spray. Pharmaceutically acceptable salts, solvates and hydrates of the particles disclosed herein are also useful in the method of the disclosure and in pharmaceutical compositions of the disclosure.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil) and injectable organic esters such as ethyl oleate. Proper fluidity can be maintained, for example, by the use of a coating such as lecithin, by the maintenance of the required particle size in the case of dispersions and by the surfactants.

These compositions may also contain adjuvants such as preserving, emulsifying, and dispensing agents. Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the particles are admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, capsules, pills, and granules can be prepared with coatings and shells, such as enteric coatings and others well known in the art. They may contain opacifying agents, and can also be of such composition that they release the particles or compounds in a certain part of the intestinal tract in a delayed manner. Examples of embedding compositions which can be used are polymeric substances and waxes. The particles can also be used in micro-encapsulated form, if appropriate, with one or more of the above-mentioned excipients. Controlled slow release formulations are also preferred, including osmotic pumps and layered delivery systems.

Liquid dosage forms for oral administration include pharmaceutically acceptable emulsions, solutions, suspensions, syrups, and elixirs. In addition to the particles, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Compositions for rectal administrations are preferably suppositories which can be prepared by mixing the particles of the present disclosure with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of particles of this disclosure include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this disclosure.

Pharmaceutical compositions typically comprise an effective amount of particles disclosed herein and a suitable pharmaceutical acceptable carrier. The preparations can be prepared in a manner known per se, which usually involves mixing the particles according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design.

Generally, for pharmaceutical use, the particles can be formulated as a pharmaceutical preparation comprising particles and at least one pharmaceutically acceptable carrier, diluent or excipient and/or adjuvant, and optionally one or more further pharmaceutically active compounds.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of particles of the disclosure e.g., about 10, 25, 50, 100, 200, 300 or 400 mg per unit dosage.

EXAMPLES

Formulation of DBA Platinum Nanoparticles

Figure 1:
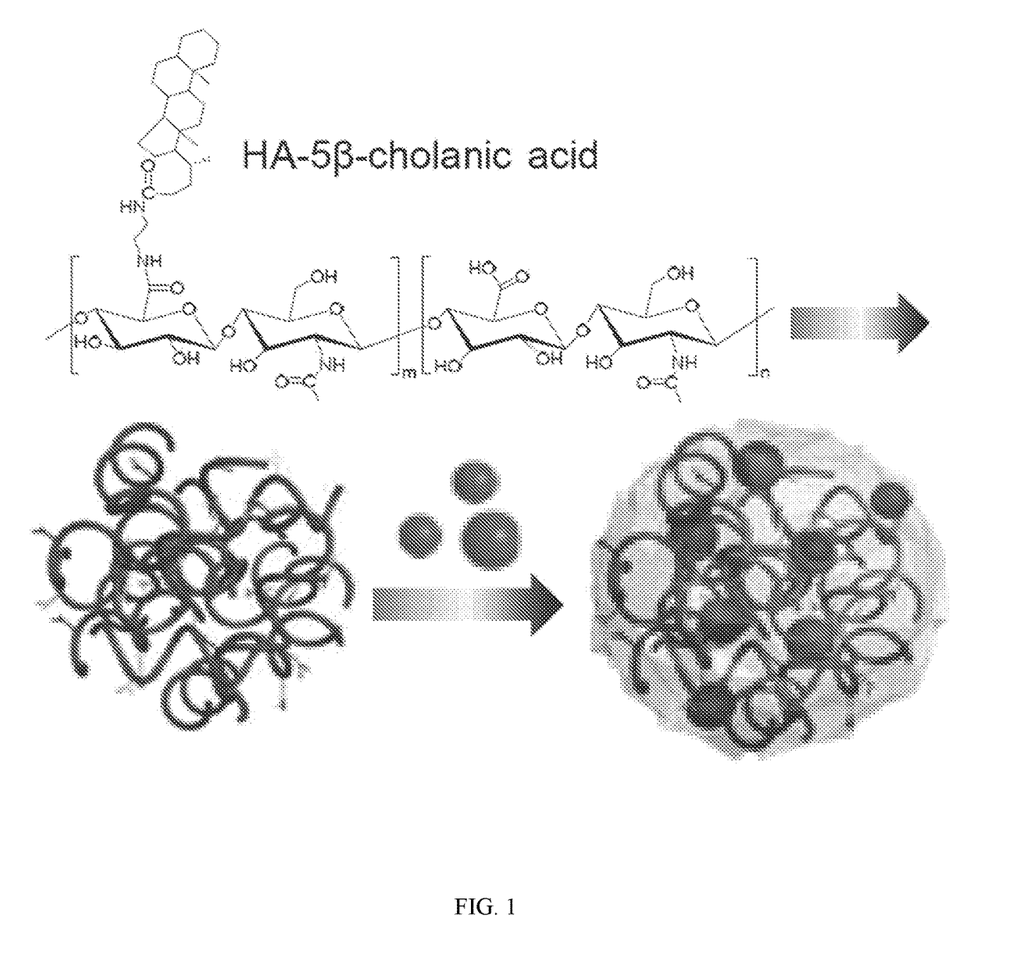
FIG. 1 illustrates the formulation of DBA Palladium HA nanoparticles. Hyaluronic Acid (HA)-5β-cholanic acid conjugate was synthesized by linking the carboxyl group of HA with the amino group on 5β-cholanic acid in the presence of EDC and NHS. HA nanoparticle/Tris DBA-Pd complex was prepared under high pressure homogenizer to encapsulate the Tris DBA-Pd into a more soluble HANP/drug complex.

Hyaluronic Acid (HA)-5β-cholanic acid conjugate was synthesized by linking the carboxyl group of HA with the amino group on 5β-cholanic acid in the presence of EDC and NHS (FIG. 1). Hyaluronic Acid nanoparticles/Tris-DBA palladium were prepared. Water-insoluble Tris DBA-Pd was physically encapsulated into the hydrophobic cavities by a high-pressure homogenizer. This allowed for the dispersion of Tris DBA-Pd under physiological conditions. After freeze-drying, 40 mg of HANPs were dispersed in 8 mL of distilled water and 10 mg of Tris DBA-Pd was dissolved in 2 mL dimethyl sulfoxide (DMSO). The Tris DBA-Pd solution was slowly added into the HANP in high pressure homogenizer and homogenized for 5 min. Finally, the resulting mixture was dialyzed for 4 hours against an excess amount of distilled water to remove unloaded drugs and organic solvent, followed by lyophilization.

Figure 2:
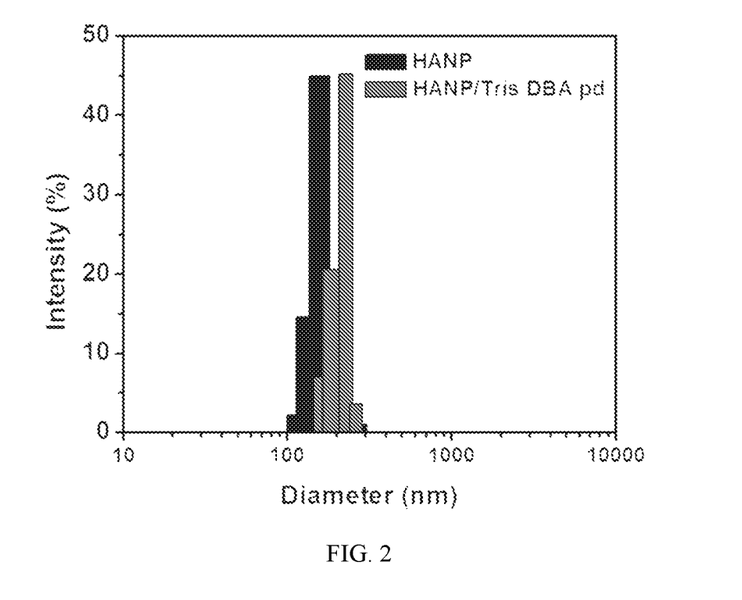
FIG. 2 shows data on the size distribution of empty hyaluronic acid nanoparticles and Tris DBA-Pd loaded nanoparticles. Empty HANPs had an average size of 180±32 nm while loaded Tris DBA-Pd HANPs had an average size of 204±25 nm indicating successful drug loading.

Compared to free Tris DBA-Pd that immediately precipitated in water, FBS, and cell culture media, Tris DBA-Pd HANP presented good dispersion in these buffers. The results indicated that Tris DBA-Pd was loaded into the interior of the HANP successfully to form Tris DBA-Pd HANPs with excellent solubility and stability in physiological buffers. To verify the encapsulation of Tris DBA-Pd, the size changes were compared before and after loading. Particles synthesized with Tris DBA-Pd revealed a 20 nm increase in average diameter, which is attributed to the encapsulation of Tris DBA-Pd inside the HANPs (FIG. 2).

An anti-Insulin-like Growth Factor-1 Receptor (IGF1R) monoclonal antibodies (Dalotuzumab) were conjugated onto the surface of HANP mediated by ethyl-3-dimethylaminopropyl carbodiimide (EDAC) and N-hydroxysulfosuccinimide (sulfo-NHS). The DBA encapsulation was verified and calculated by HPLC.

Palladium Based Nanoparticles for the Treatment of Advanced Melanoma

Tris DBA-Pd was successfully loaded into hyaluronic acid nanoparticles, with and without antibodies to IGF1R (FIG. 1). Synthesized particles ranged from an average of 180 nm in diameter for empty HANPs to approximately 204 nm in diameter for Tris DBA-Pd loaded nanoparticles (FIG. 2). This increase in diameter of average particle size indicates the successful conjugation of Tris DBA-Pd into the nanoparticles. To confirm the encapsulation of Tris-palladium, 1 mg of HANP/Tris DBA complex was dissolved in 1 mL water and subjected to HPLC (C18, 5 µm, 250×4.6 mm) with a linear gradient from 20% to 95% acetonitrile/water (0.1% TFA) at a flow rate of 1 mL·min-1 and the detection wavelength at 224 nm. The standard curve is calculated as $y=461.74x+3.5848$ ($R^2=0.9999$), according to which the efficiency of Tris DBA encapsulation into HANP was calculated. Tris DBA (0.16 mg) was detected in HANP/Tris DBA complex, indicating that 80% of Tris DBA was encapsulated into HANP drug delivery system.

Figure 3:
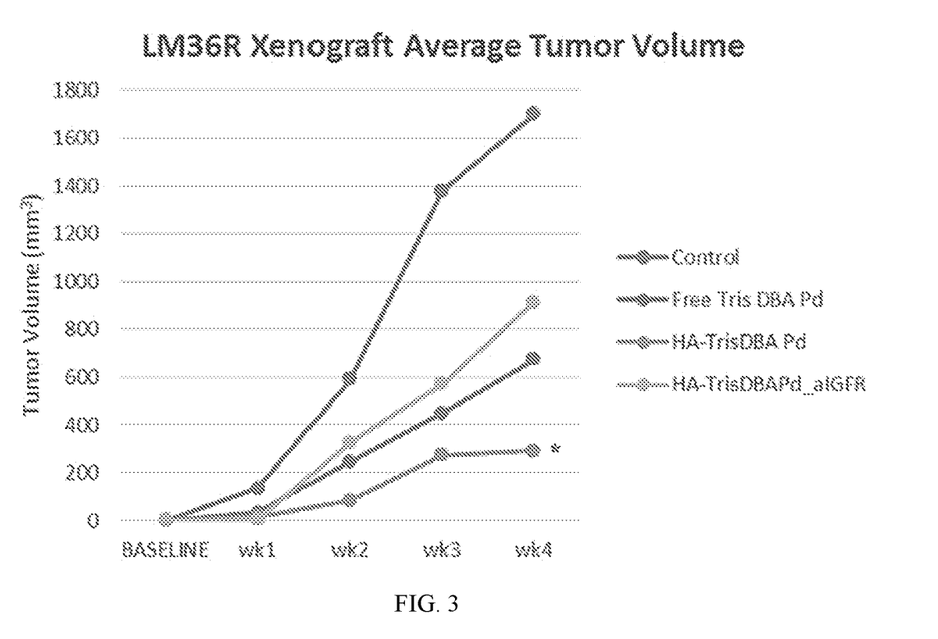
FIG. 3 shows data using hyaluronic acid nanoparticles with Tris DBA-Pd indicating efficacy in vemurafenib-resistant melanoma. Nude male mice were inoculated with LM36R ($5.0\times10^5$ cells), a human cell line of melanoma that is resistant to vemurafenib, and then treated with HANPs over the course of four weeks. When compared to the other groups, hyaluronic acid nanoparticles conjugated with Tris DBA-Pd (Tris DBA-Pd HANP) proved most effective. Interestingly, HANPs with Tris DB-Pd proved even more effective than free Tris DBA-Pd and HANPs with Tris DBA-Pd conjugated with an IGF1R antibody (n=5 per group) (Asterisk indicates significance with a p-value of 0.048 at week 4).

Of the experimental treatment groups, hyaluronic acid-based nanoparticles containing only Tris DBA-Pd, (Tris DBA-Pd HANP, were superior to other groups in inhibiting the growth of LM36R in nude mice with a significant p-value of 0.048 at the fourth week. Surprisingly, the Tris DBA-Pd HANP particles alone were more effective than those conjugated to antibodies to IGF1R, and tumor growth appeared to plateau at week three while the other groups continued their exponential growth (FIG. 3). Mice were sacrificed beyond 4 weeks due to reaching endpoint.

Immunohistochemistry was performed to qualitatively assess expression of target genes. A striking reduction of CD44 expression was noted in tumors treated with the Tris DBA-Pd HANP compared with other treatment arms. To assess the impact of our treatments on IGF1R expression, IHC was used to stain the tumor xenografts with antibodies against IGF1R. It was observed that tumors expressed IGF1R and that Tris DBA-Pd HANPs coupled with anti-IGF1R antibodies decreased the intensity of IGF1R staining more so than the other groups, suggesting that targeting was occurring.

FGF2 was found to be downregulated in our gene arrays as a result of treatment. The impact of free Tris DBA-Pd and Tris DBA-Pd nanoparticles on FGF2 expression was assessed within tumor xenografts using immunohistochemistry (IHC). The HANPs decreased IHC staining intensity for FGF2 independent of whether the nanoparticles were coupled to anti-IGF1R antibodies. This suggests that palladium containing HANPs downregulate FGF2 expression in our tumor model. FGF2 has been previously implicated as a melanoma growth factor and immunosuppressive agent.

Figure 4:
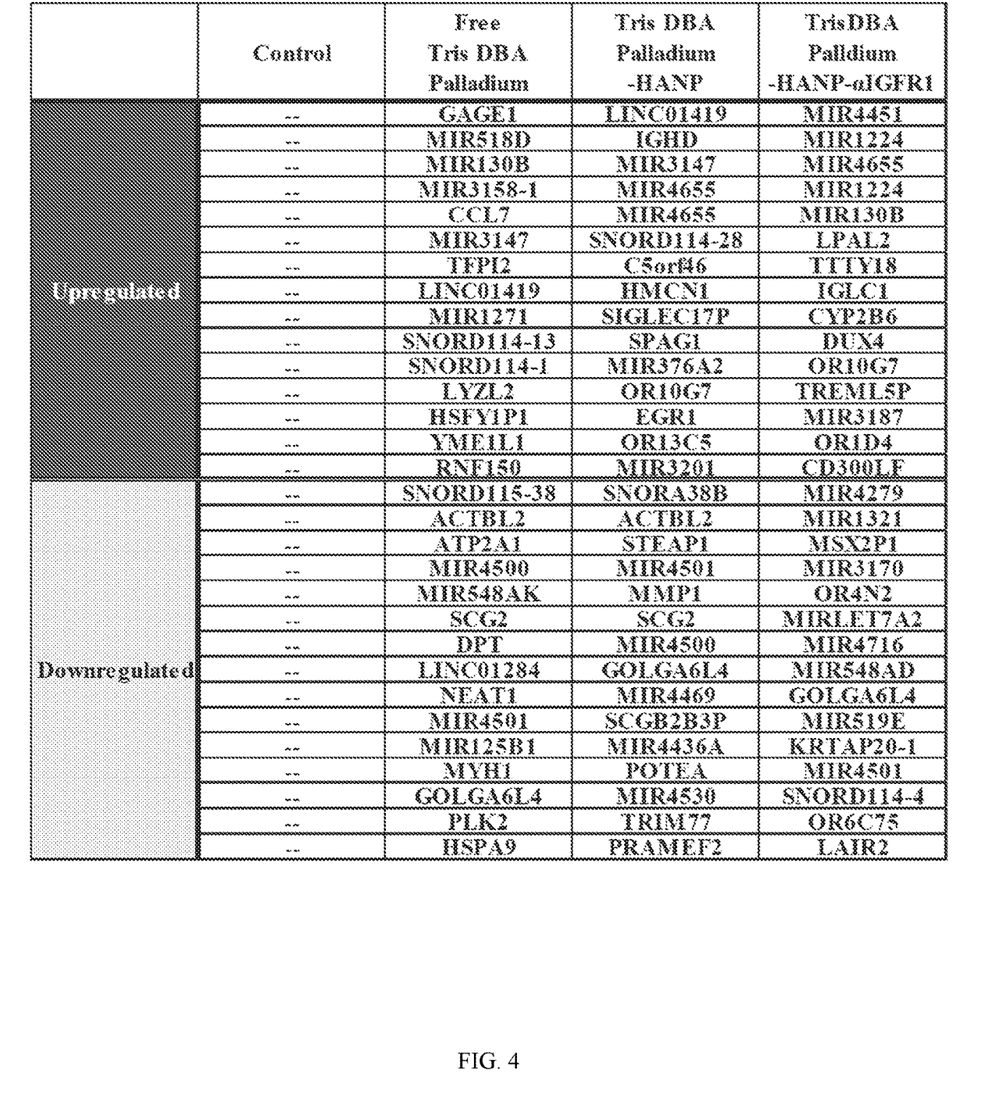
FIG. 4 shows a list of the most up- and down-regulated gene from microarray RNA analysis after exposure to nanoparticles in expression in LM36R xenograft tumor.

Gene array was performed on all tumors. Distinct and reproducible heat maps were generated by each arm of treatment, thus demonstrating mechanistically distinct effects of nanoparticles versus free drugs. The differences were also observed by examination of the top up and down-regulated genes (FIG. 4). Notably, there were large differences in between the three palladium arms in terms of gene expression. This is of great importance, because it demonstrates that different targeting modalities of the same drug can have very different effects on tumor signaling. By varying the delivery process of a single drug, one might be able to prevent resistance. Interestingly, one of the most upregulated genes in the Tris DBA-Pd HANP arm is IGHD, an immune marker which has been noted to be upregulated in melanomas that are responsive to ipilimumab. Other upregulated genes include SPAG1, which is a cancer antigen. Actin beta 2 like is downregulated in two of the palladium arms, and this gene has recently been shown to be upregulated in colon cancer.

The efficacy of Tris DBA-Pd nanoparticles was assessed against LM36R, a highly aggressive human melanoma xenograft, which is BRAF mutant and resistant to the BRAF inhibitor, vemurafenib. Tris DBA-Pd was incorporated into hyaluronic acid containing nanoparticles, either containing IGF-1 to target IGF1R expressing melanomas, or hyaluronic acid particles not containing IGF-1. Of interest, hyaluronic acid itself targets CD44, a cell surface marker associated with highly malignant behaviors in many solid malignancies. The Tris DBA-Pd nanoparticles that do not contain anti-IGF-1 antibodies are the most effective in vivo. In addition, it causes depletion of CD44+ tumor cells. In vivo analysis of treated tumors reveals intriguing targets. The transcription factor Egr-1 is upregulated by HANP Tris DBA and upregulation of Egr-1 confers radiation sensitivity upon melanoma. Of interest, one of the most upregulated genes in the Tris DBA-Pd HANP arm is IGHD, an immune marker which has been noted to be upregulated in melanomas that are responsive to ipilimumab. HMCN1 is also induced by Tris DBA HANP and high-level expression of this molecule is associated with improved prognosis in human melanoma. SCG2 (secretogranin 2) is downregulated by both free tris DBA and Tris DBA HANP, and low expression of SCG2 is associated with improved prognosis in human melanoma. Secretogranin 2 encodes a precursor for secretoneurin, which promotes migration of melanoma cells.

Data herein indicates there is no overlap between resistance to BRAF inhibitors (vemurafenib) and Tris DBA-Pd. Tris DBA-Pd can be effectively packaged in hyaluronic acid containing nanoparticles. While free Tris DBA showed efficacy in this model, the physical characteristics of free Tris DBA, namely the variability in particle size, might preclude development of the free compound as an intravenous formulation. The nanoparticle formulation allows uniform particle preparation. By targeting a pathway one can expand the indication of this drug to a wide variety of tumors. Tris DBA-Pd particles with hyaluronic acid alone was superior to that of the particles containing antibody to IGF1R and hyaluronic acid. One possibility is that targeting both IGF1R (IGF-1) and CD44 (hyaluronic acid) may cause competition or steric hindrance. There is also a possibility that these nanoparticles are reaching other cells containing IGF1R thus diverting its antitumorigenic effects.

In Vivo Studies

Vemurafenib-resistant LM36R human melanoma cells were inoculated ($5.0 \times 10^5$ cells/mouse) into the right flank of athymic Nu/Nu nude male mice (Crl:NU-Foxn1$^{nu}$ strain code 088)) n=5 per group, and progression of tumor was recorded using the volume model of length×(width)×0.52. Mice were split into four groups consisting of a control (empty HANP), free Tris DBA-Pd, HANP with Tris DBA-Pd, and HANP with Tris DBA-Pd and aIGF1R antibody. Free Tris DBA-Pd was first dissolved in DMSO and then mixed with Kolliphor EL™. At last, the mixture was diluted by H$_2$O before injection at concentration of 1 mg/mL of DBA. The ratio of DMSO, Kolliphor EL™ and H$_2$O was controlled as 1:2:7 (v/v). The treatments were administered through bi-weekly tail vein injections over the course of 4 weeks (5 mg of drug/kg per injection). Tumor samples were analyzed for CD44 (hyaluronate receptor) expression by immunohistochemistry.

Gene Array and Whole-Transcriptome Expression Analysis.

RNA Extraction and QC: RNA was extracted using the Qiagen miRNEasy™ kit with on column DNAse treatment. Tissue was lysed and homogenized in Qiazol™ with a rotor-stator probe homogenizer for 40 seconds or until fully disrupted (1 ml Qiazol™ per 100 mg of tissue). RNA was eluted in 50 ul nuclease free water. One microliter was used to determine OD (optical density) values on a Nanodrop 1000. One microliter was used to assess sample profiles on the Agilent 2100 using the RNA 6000 Nano assay. Total RNA (250 ng) was amplified and labeled using the ThermoFisher Scientific Illuina™ TotalPrep™ RNA Amplification kit. Labeled cRNA was hybridized to Illumina HT12™ bead array. Image acquisition and data extraction were performed.

The invention claimed is:

1. A particle comprising dibenzylideneacetone palladium and hyaluronic acid comprising a lipid covalently conjugated to the hyaluronic acid, wherein the lipid is a polycyclic hydrocarbon.

2. The particle of claim 1, wherein the lipid is an amide conjugated 5(beta) cholanic acid.

3. The particle of claim 1 made by a process of mixing dibenzylideneacetone palladium and the lipid covalently conjugated to the hyaluronic acid in a homogenizer providing a particle that is a mixture of the dibenzylideneacetone palladium and a hyaluronic acid conjugate.

4. The particle of claim 3, wherein the process of mixing is forcing the mixture of the dibenzylideneacetone palladium and the hyaluronic acid conjugate through a narrow gap at a pressure above 5 MPa.

5. A pharmaceutical composition comprising a particle of claim 1 and a pharmaceutically acceptable excipient.

6. The pharmaceutical composition of claim 5 in the form of a tablet, pill, capsule, gel, gel capsule or cream.

7. The pharmaceutical composition of claim 5 in the form of a sterilized pH buffered aqueous salt solution or a saline phosphate buffer between a pH of 6 to 8, optionally comprising a saccharide or polysaccharide.

8. The pharmaceutical composition of claim 5 in solid form surrounded by an enteric coating.

9. The pharmaceutical composition of claim 5, wherein the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, corn starch, carnauba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

10. A method of treating cancer comprising administering an effective amount of particles of claim 1 to a subject in need thereof.

11. The method of claim 10, wherein the particles are administered in combination with a second therapeutic agent.

12. The method of claim 10, wherein the cancer is selected from multiple myeloma, bladder cancer, lung cancer, breast cancer, melanoma, colon and rectal cancer, non-Hodgkin lymphoma, Burkett lymphoma, endometrial cancer, pancreatic cancer, kidney cancer, prostate cancer, leukemia, thyroid cancer, and brain cancer.

13. The method of claim 10, wherein the subject is diagnosed with CD44 positive cancer cells.

14. The method of claim 10, wherein the particles are administered in combination with ipilimumab.

15. The particle of claim 4, wherein the process of mixing is forcing the mixture of dibenzylideneacetone palladium and the hyaluronic acid conjugate through a narrow gap at a pressure above 50 MPa.

16. The particle of claim 4, wherein the process of mixing is forcing the mixture of dibenzylideneacetone palladium and the hyaluronic acid conjugate through a narrow gap at a pressure above 100 MPa.

17. The particle of claim 4, wherein the process of mixing is forcing the mixture of dibenzylideneacetone palladium and the hyaluronic acid conjugate through a narrow gap at a pressure above 150 MPa.

18. The particle of claim 4, wherein the process of mixing is forcing the mixture of dibenzylideneacetone palladium and the hyaluronic acid conjugate through a narrow gap at pressure above 200 MPa.

19. The particle of claim 4, wherein the process of mixing is forcing the mixture of dibenzylideneacetone palladium and the hyaluronic acid conjugate through a narrow gap at a pressure above 250 MPa.

20. The particle of claim 4, wherein the process of mixing is forcing the mixture of dibenzylideneacetone palladium and the hyaluronic acid conjugate through a narrow gap at a pressure above 350 MPa.

* * * * *